US012618212B2

(12) United States Patent
Kirchmair et al.

(10) Patent No.: US 12,618,212 B2
(45) Date of Patent: May 5, 2026

(54) SNOWGROOMER AND METHOD FOR CONTROLLING A SNOWGROOMER

(71) Applicant: PRINOTH S.P.A., Vipiteno (IT)

(72) Inventors: Martin Kirchmair, Vipiteno (IT); Stephan Muehlsteiger, Vipiteno (IT); Andreas Silbernagl, Vipiteno (IT); Alberto Paoletti, Vipiteno (IT)

(73) Assignee: PRINOTH, S.P.A. (IT)

( * ) Notice: Subject to any disclaimer, the term of this patent is extended or adjusted under 35 U.S.C. 154(b) by 471 days.

(21) Appl. No.: 18/027,233

(22) PCT Filed: Sep. 24, 2021

(86) PCT No.: PCT/IB2021/058733
§ 371 (c)(1),
(2) Date: Mar. 20, 2023

(87) PCT Pub. No.: WO2022/064443
PCT Pub. Date: Mar. 31, 2022

(65) Prior Publication Data
US 2023/0366160 A1 Nov. 16, 2023

(30) Foreign Application Priority Data

Sep. 24, 2020 (IT) ......................... 102020000022564

(51) Int. Cl.
*E01H 4/02* (2006.01)
*G01N 33/18* (2006.01)
(52) U.S. Cl.
CPC ............... *E01H 4/02* (2013.01); *G01N 33/18* (2013.01); *G01N 33/1873* (2024.05)
(58) Field of Classification Search
CPC .... E01H 4/02; E01H 5/02; E01H 5/06; E01H 5/061; E01H 5/063; G01N 33/18; G01N 33/1873
See application file for complete search history.

(56) References Cited

U.S. PATENT DOCUMENTS

| | | | | |
|---|---|---|---|---|
| 6,698,112 B2 * | 3/2004 | Grobler | ..................... | E01H 4/02 |
| | | | | 37/219 |
| 2003/0051376 A1 * | 3/2003 | Lassonde | .................. | E01H 4/02 |
| | | | | 37/348 |

FOREIGN PATENT DOCUMENTS

| | | |
|---|---|---|
| CA | 2365602 A1 | 8/2001 |
| CN | 109629503 A | 4/2019 |

(Continued)

OTHER PUBLICATIONS

Office Action issued Feb. 11, 2026, in corresponding Chinese application No. 202111122332.3.

*Primary Examiner* — Joseph M Rocca
*Assistant Examiner* — Robert E Pezzuto
(74) *Attorney, Agent, or Firm* — Aldo Noto, Esq.; Rimon PC

(57) ABSTRACT

A snow groomer vehicle comprising: a frame (2) extending along a longitudinal axis (70); a tiller assembly (9) connected to the frame (2) by a connecting device (21), preferably the tiller assembly (9) comprising a tiller (9a) and a finisher (9b); at least one control device (17) coupled to the tiller assembly (9) and configured to control at least two parameters of the tiller assembly the control device (17) comprising a memory configured to store at least two groups of values (N, M), preferably four groups of values (N, M, P, Q), relating to the at least two parameters (A, B), wherein each group of values (N, M) includes at least one value for each of the at least two parameters (A, B); the control device (17) being configured to receive the selection of a group of values of the at least two groups of values (N, M) and control the at least two parameters of the tiller assembly (9) according to the values of the selected group of values (N; M).

22 Claims, 5 Drawing Sheets

(56)         References Cited

FOREIGN PATENT DOCUMENTS

| CN | 110184986 A | 8/2019 |
| DE | 10045522 A1 | 3/2002 |
| DE | 10045524 A1 | 3/2002 |
| EP | 1286000 A1 | 2/2003 |
| IT | 201900002017 A1 | 8/2020 |
| WO | 2020065607 A1 | 4/2020 |
| WO | 2020104860 A1 | 5/2020 |

* cited by examiner

|  | A | B | C | D | E |
|---|---|---|---|---|---|
| x' | $N'_A$ $M'_A$ $P'_A$ $Q'_A$ $\cdots$ $Z'_A$ | $N'_B$ $M'_B$ $P'_B$ $Q'_B$ $\cdots$ $Z'_B$ | $N'_C$ $M'_C$ $P'_C$ $Q'_C$ $\cdots$ $Z'_C$ | $N'_D$ $M'_D$ $P'_D$ $Q'_D$ $\cdots$ $Z'_D$ | $N'_E$ $M'_E$ $P'_E$ $Q'_E$ $\cdots$ $Z'_E$ |
| x'' | $N''_A$ $M''_A$ $P''_A$ $Q''_A$ $\cdots$ $Z''_A$ | $N''_B$ $M''_B$ $P''_B$ $Q''_B$ $\cdots$ $Z''_B$ | $N''_C$ $M''_C$ $P''_C$ $Q''_C$ $\cdots$ $Z''_C$ | $N''_D$ $M''_D$ $P''_D$ $Q''_D$ $\cdots$ $Z''_D$ | $N''_E$ $M''_E$ $P''_E$ $Q''_E$ $\cdots$ $Z''_E$ |

FIG. 5

SNOWGROOMER AND METHOD FOR CONTROLLING A SNOWGROOMER

CROSS-REFERENCE TO RELATED APPLICATIONS

This patent application claims priority from Italian Patent Application No. 102020000022564 filed on Sep. 24, 2020, the entire disclosure of which is incorporated herein by reference.

TECHNICAL FIELD

The present invention relates to a snow groomer vehicle and a method for controlling a snow groomer vehicle.

BACKGROUND ART

As is known, the preparation of ski slopes requires ever-increasing care, both for safety reasons and because modern tools can be much better used on surfaces which are regular, without marked roughness and as homogeneous as possible. The snowpack is processed by snow groomer vehicles, which are equipped with special tools for this purpose. In particular, a snow groomer vehicle generally comprises a shovel or blade at the front, and a tiller and a finisher at the rear. The rear tool with the tiller and the finisher allows the desired finish of the snowpack surface to be achieved.

However, the quality of the preparation of the slopes is currently largely entrusted to the skill and experience of the operators of the snow groomer vehicles, who have almost complete control over the working tools. The obtainable results, which are obviously affected by a non-negligible subjective component, are therefore scarcely repeatable and cannot be easily optimized. This results, on the one hand, in uneven conditions, beyond what the objective environmental factors would allow, and, on the other hand, in a greater expenditure of time and resources because the processing steps are not carried out optimally.

Instead, more uniformity of results would be desirable, especially to make up for the more limited capabilities of less experienced operators.

DISCLOSURE OF INVENTION

The object of the present invention is to provide a snow groomer vehicle and a method for controlling a snow groomer vehicle, which allow the limitations described above to be overcome, or at least mitigated.

Therefore, according to the present invention, there is provided a snow groomer vehicle comprising: a frame extending along a longitudinal axis; a tiller assembly connected to the frame by a connecting device, preferably the tiller assembly comprising at least a tiller and a finisher; at least one control device coupled to the tiller assembly and configured to control at least two parameters of the tiller assembly, preferably five parameters, selected from a group comprising the following parameters of the tiller assembly: speed and/or direction of rotation of the shaft; depth and/or cutting angle of the tiller assembly, preferably of the tiller; position of the tiller assembly along a vertical axis; mode for adjusting the position of the tiller assembly along a vertical axis, preferably among: a mode wherein the tiller assembly is in a fixed position, a mode wherein the tiller assembly exerts a certain pressure on the snowpack in addition to its own weight or by subtraction from its own weight and said pressure value exerted, and a mode wherein the tiller assembly is in a floating position, in particular in the floating position it follows the snowpack; position of the wings, open or closed; volume of a working chamber of the tiller; position of the tiller in relation to a horizontal plane; mode of adjustment of the position of the tiller in relation to a horizontal plane, preferably between a mode wherein the tiller assembly is in a fixed position, and a mode wherein the tiller assembly is in a floating position, in particular in the floating position it follows the movements of the snow groomer vehicle; and position of the finisher;

the control device comprising a memory configured to store at least two groups of values, preferably four groups of values, relating to the at least two parameters, wherein each group of values includes at least one value for each of the at least two parameters;

the control device being configured to receive the selection of a group of values of the at least two groups of values and control the at least two parameters of the tiller assembly according to the values of the selected group of values.

Thanks to the present invention, the use of said snow groomer is simpler for an operator and the result of the processing is better even for less experienced operators.

In addition, the control device is configurable so that it can automatically select one of the at least two groups of values based on the detection of other parameters via sensors or on the position of the snow groomer vehicle in a ski resort or on a command received from remote or on a pre-set setting.

Therefore, the group of values can be automatically selected without the intervention of the operator and, consequently, further simplifying his/her work. This ensures a better snowpack processing result that is less dependent on the experience of the snow groomer operator.

According to a further aspect of the invention, there is also provided a control method for controlling a snow groomer vehicle; the snow groomer vehicle comprising: a frame extending along a longitudinal axis; a tiller assembly connected to the frame by a connecting device, preferably the tiller assembly comprising a tiller and a finisher; the method comprising the steps of: controlling at least two parameters of the tiller assembly, preferably five parameters, selected from a group comprising the following parameters of the tiller assembly: speed and/or direction of rotation of the shaft; depth and/or cutting angle of the tiller assembly, preferably of the tiller; position of the tiller assembly along a vertical axis; mode for adjusting the position of the tiller assembly along a vertical axis, preferably among: a mode wherein the tiller assembly is in a fixed position, a mode wherein the tiller assembly exerts a certain pressure on the snowpack in addition to its own weight or by subtraction from its own weight and said pressure value exerted, and a mode wherein the tiller assembly is in a floating position, in particular in the floating position it follows the snowpack; position of the wings, open or closed; volume of a working chamber of the tiller; position of the tiller in relation to a horizontal plane; mode of adjustment of the position of the tiller in relation to a horizontal plane, preferably between a mode wherein the tiller assembly is in a fixed position, and a mode wherein the tiller assembly is in a floating position, in particular in the floating position it follows the movements of the snow groomer vehicle; and position of the finisher;

storing at least two groups of values, preferably four groups of values, relating to the at least two parameters, wherein each group of values includes at least one value for each of the at least two parameters;

receiving the selection of a group of values of the at least two groups of values;

and controlling the parameters of the tiller assembly according to the values of the selected group of values.

BRIEF DESCRIPTION OF THE DRAWINGS

Further features and advantages of the present invention will be apparent from the following description of non-limiting embodiments thereof, with reference to the figures of the accompanying drawings, wherein:

FIG. 5 is a diagram showing groups of values of parameters controlled by a control device of the snow groomer vehicle 1.

BEST MODE FOR CARRYING OUT THE INVENTION

Figure 1:
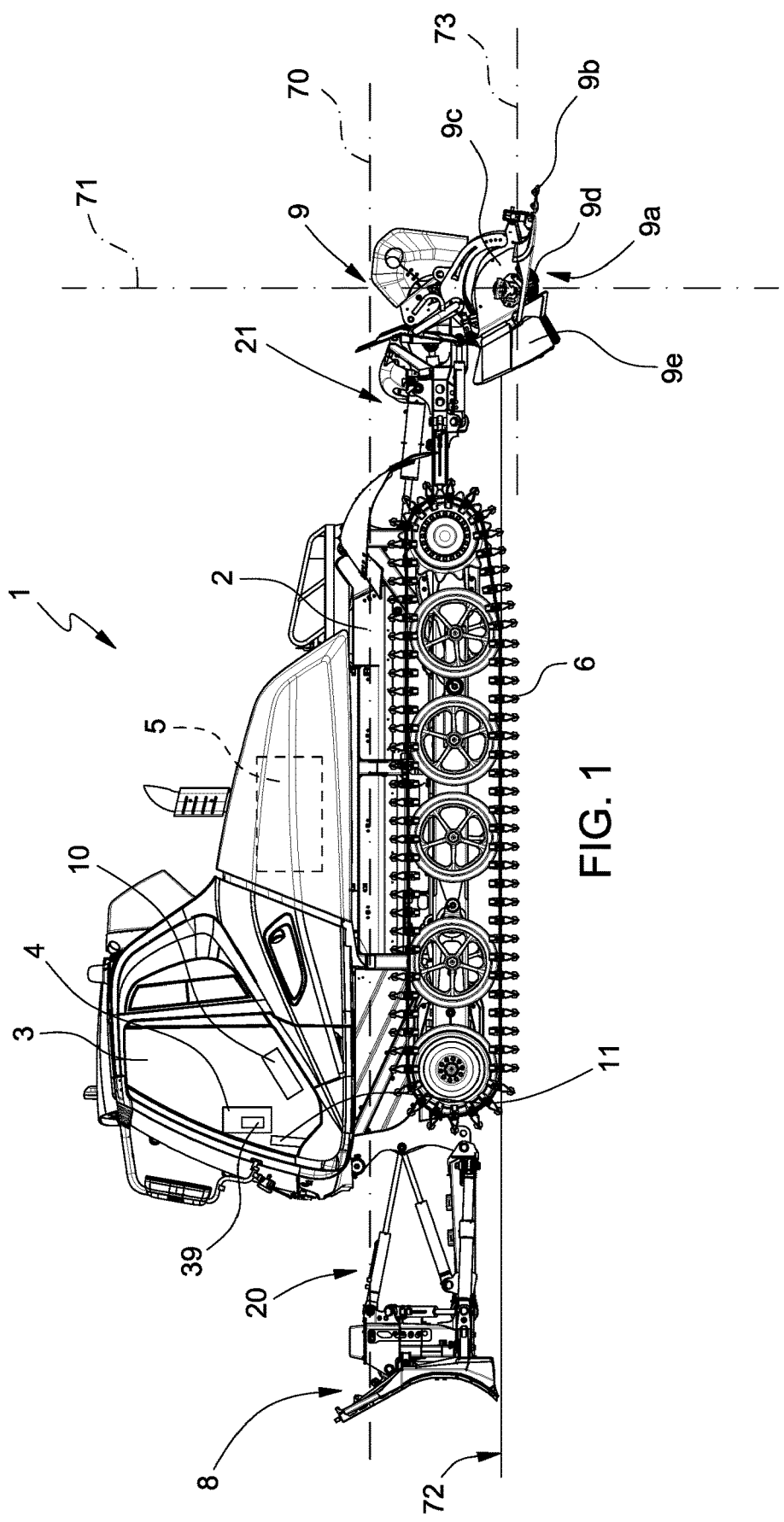
FIG. 1 is a side view of a snow groomer vehicle in accordance with an embodiment of the present invention.
Figure 2:
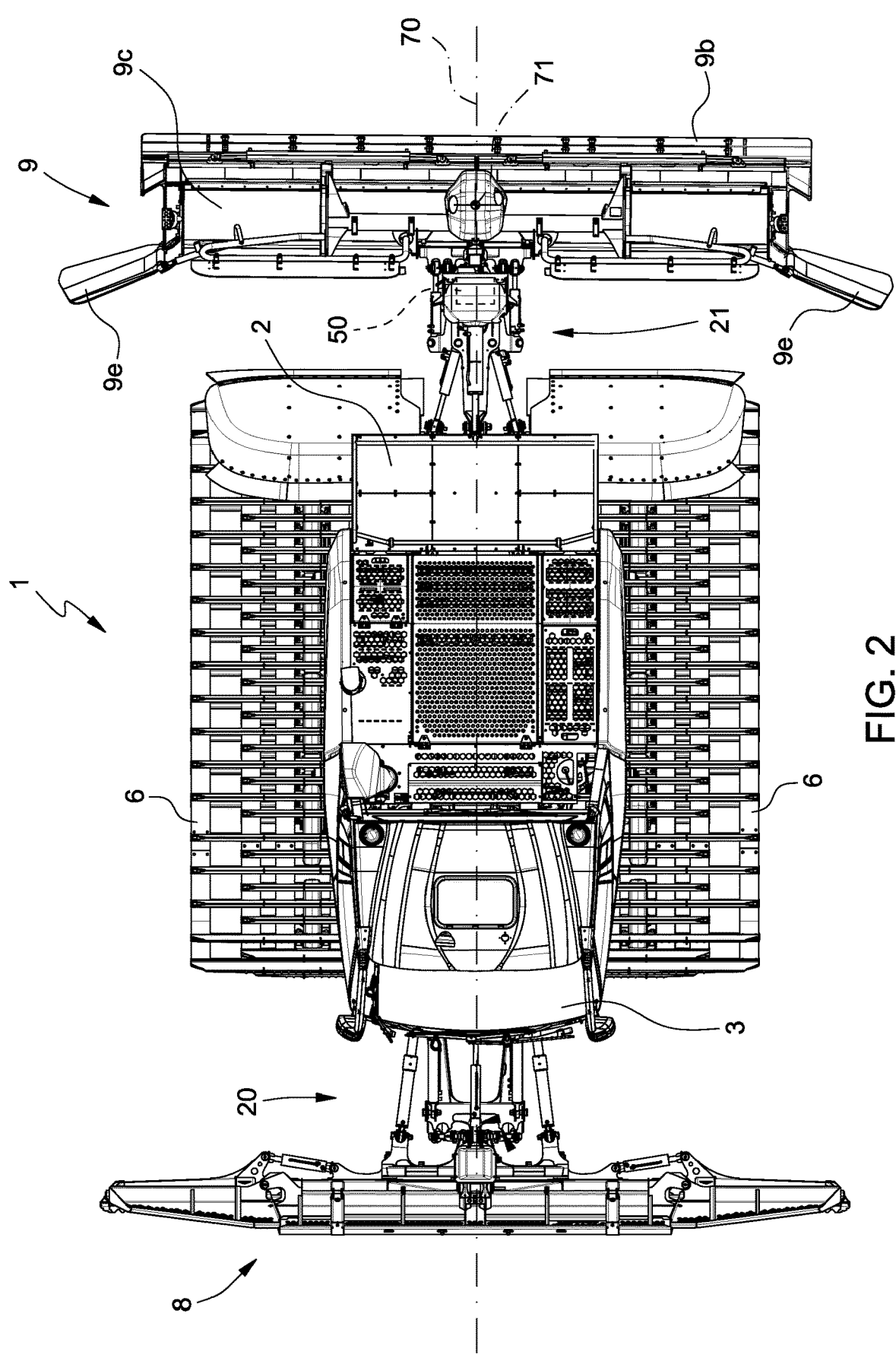
FIG. 2 is a top plan view of the snow groomer vehicle in FIG. 1.
Figure 3:
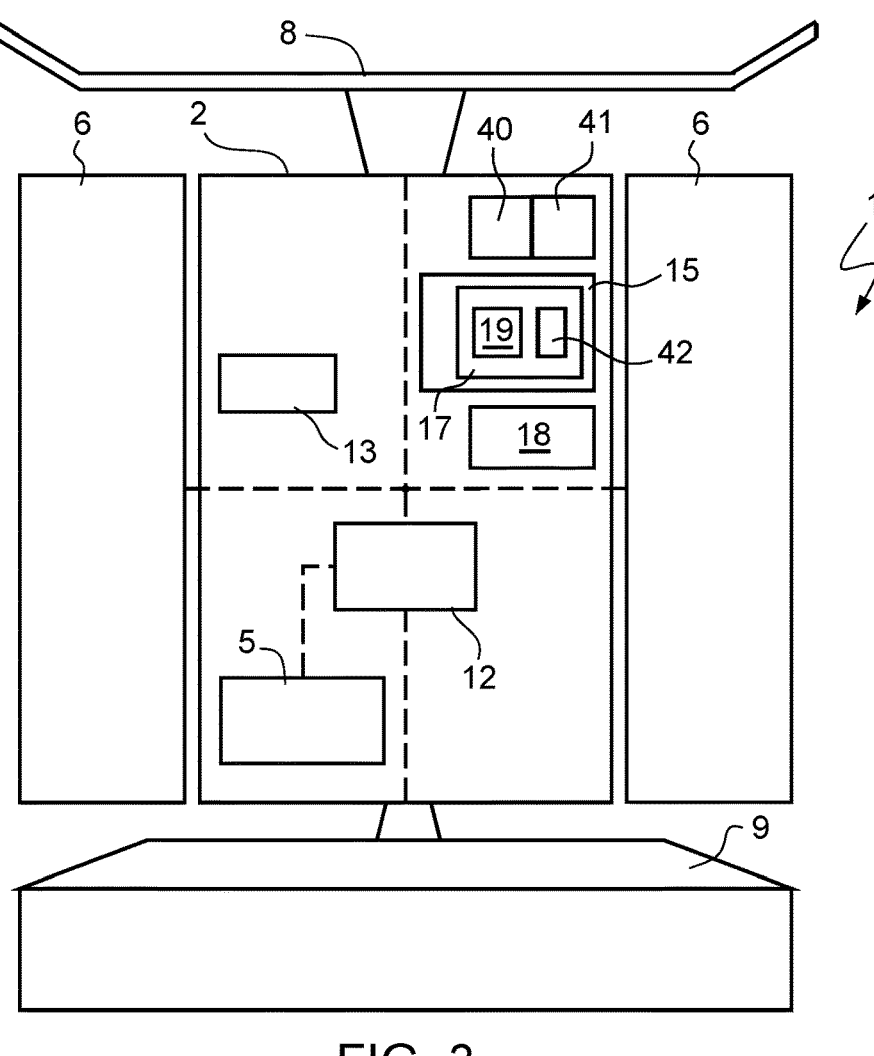
FIG. 3 is a simplified block diagram of the snow groomer vehicle in FIG. 1.
Figure 4:
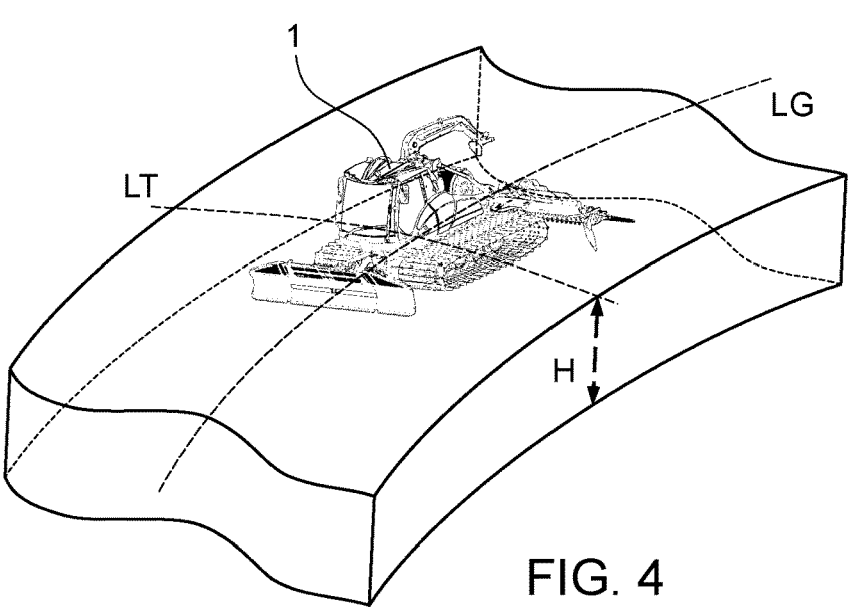
FIG. 4 shows coordinates detectable by a component of the snow groomer vehicle in FIG. 1.

With reference to FIGS. 1 to 3, a snow groomer vehicle according to an embodiment of the present invention is designated as a whole by the reference numeral 1 and comprises a frame 2, which extends along a longitudinal axis 70, a driver's cab 3, and a drive unit 5, for example, an internal combustion engine. The driver's cab 3 and the drive unit 5 are housed on the frame 2. The snow groomer vehicle 1 is also provided with a pair of tracks 6 and user devices, including a shovel or blade 8, supported by the frame 2 at the front, and a tiller assembly 9 comprising a tiller 9a and preferably a finisher 9b, supported by the frame 2 at the rear. There may also be a winch assembly, not shown here.

The drive unit 5 supplies the power required for the operation of the snow groomer vehicle 1, and in particular to the tracks 6 and the user devices 8 and 9.

The power transmission 12 can be hydraulic or electric or a combination of both.

The drive unit 5 may be an electric motor with a rechargeable battery instead of an internal combustion engine. Alternatively, the drive unit 5 may be a hybrid engine comprising an internal combustion engine and an electric motor connected in series or in parallel. In another embodiment, the drive unit 5 may be a hydrogen powered fuel cell engine.

The tiller 9a particularly comprises a toothed rotating shaft 9d and a protective guard 9c which is arranged above the rotating shaft 9d. The area between the protective guard 9c and the rotating shaft 9d is designated as the working chamber and is configured to have a variable volume. In particular, the tiller 9a comprises a device for varying the distance between the rotating shaft 9d and the protective guard 9c or for varying the position of the finisher 9b, in this way the volume of the working chamber can be adjusted. This device can act on the rotating shaft 9d by modifying its position or it can act on the protective guard 9c by modifying its position or it can act on the finisher 9b by varying its position. By varying the working chamber, a different tilling of the processed snowpack is obtained.

The tiller assembly 9 comprises two side wings 9e arranged laterally to the protective guard 9c.

In one embodiment, not shown in the accompanying figures, the tiller assembly 9 comprises two tillers 9a which are connected to each other by means of a preferably universal joint. In this embodiment, each of the two tillers 9a comprises a toothed rotating shaft 9d and a protective guard 9c which is arranged above the rotating shaft 9d.

A user interface is installed in the driver's cab 3, which interface allows an operator to control the movement of the snow groomer vehicle 1 and the operation of the user devices.

In particular, the snow groomer vehicle 1 comprises the user interface, which in turn comprises a travel control 10 for the movement of the snow groomer vehicle 1 for controlling the direction and speed of travel of the snow groomer vehicle 1, in particular, the travel control 10 controls the movement of the tracks 6 to define the direction and speed of movement of the snow groomer vehicle 1.

Moreover, the snow groomer vehicle 1 comprises the user interface, which in turn comprises an actuation command 11 for operating the user devices, in particular the actuation command 11 controls the user devices. In one embodiment, the actuation command 11 comprises a joystick comprising a lever, a plurality of push-buttons. In one embodiment, said joystick also comprises at least one slider and at least one mini-lever.

In particular, the actuation command 11 controls one or more of the following parameters relating to the tiller assembly 9: speed and/or direction of rotation of the shaft 9d; depth and/or cutting angle of the tiller assembly 9, preferably of the tiller 9a; position of the tiller assembly 9a along a vertical axis 71; mode for adjusting the position of the tiller assembly 9 along a vertical axis 71, preferably among: a mode wherein the tiller assembly 9 is in a fixed position, a mode wherein the tiller assembly 9 exerts a certain pressure on the snowpack 72 in addition to its own weight or by subtraction from its own weight and said pressure value exerted, and a mode wherein the tiller assembly 9 is in a floating position, in particular in the floating position it follows the snowpack 72; position of the wings 9e, open or closed; volume of a working chamber of the tiller 9a; position of the tiller 9a with respect to a horizontal plane 73; mode of adjustment of the position of the tiller 9a in relation to a horizontal plane 73 preferably between a mode wherein the tiller assembly 9 is in a fixed position, and a mode wherein the tiller assembly is in a floating position, in particular in the floating position it follows the movements of the snow groomer vehicle 1; and position of the finisher 9b.

Moreover, in the above-described embodiment wherein the tiller assembly 9 comprises two tillers 9a connected to each other by a preferably universal joint, the actuation command 11, in addition to the above, can also control, among the one or more of the parameters of the group of parameters described above, the mode of adjustment of the relative position of the two tillers 9a in the tiller assembly 9, in particular among: a mode wherein the relative position of the two tillers 9a is free and consequently the two tillers 9a are free to move independently of each other, a mode wherein the position of the two tillers 9a is fixed so that the two tillers 9a form a given angle of 180° lying in a plane oblique to the snowpack 72, in particular, the angle faces the snowpack 72, a mode wherein the position of the two tillers 9a is fixed so that the two tillers 9a form a given angle of less than 180° lying in a plane oblique to the snowpack 72, in particular, the angle faces the snowpack 72, and a mode wherein the position of the two tillers 9a is fixed so that the two tillers 9a form a given angle of more than 180° lying in a plane oblique to the snowpack 72, in particular, the angle faces the snowpack 72.

Moreover, the actuation command 11 controls the positions of the blade 8 with respect to the three Cartesian axes.

In a non-limiting embodiment, the snow groomer vehicle 1 comprises the user interface which in turn comprises a display screen 4 which is configured to show information concerning operating parameters of the snow groomer vehicle 1 and of the user devices, in particular, the blade 8 and the tiller assembly 9.

The snow groomer vehicle 1 is provided with a satellite navigation device 13, and with a control system 15.

The satellite navigation device 13, for example a GNSS ("Global Navigation Satellite System") device, is configured to determine, with centimetre precision, its three-dimensional position and orientation and, consequently, the three-dimensional position and orientation of the snow groomer vehicle 1. In practice, the satellite navigation device 13 makes it possible to determine longitude LG, latitude LT and preferably height above the ground H, in addition to the direction of travel. The height above the ground H corresponds to the thickness of the snowpack 72 at the coordinates of the satellite navigation device 13 and of the snow groomer vehicle 1. The height above the ground H, in particular, can be determined by the difference between a height detected by the satellite navigation device 13 and a height of the ground defined by a reference map with corresponding longitude LG and latitude LT. The reference map can be made using the satellite navigation device 13 in the absence of snow and stored in the satellite navigation device 13 or in the control system 15. In the first case, the height above the ground H is provided directly by the satellite navigation device 13; in the second case, the satellite navigation device 13 can provide a height with respect to a reference height (for example, sea level) and the height above the ground H is determined by the control system 15 using the reference map.

The control system 15 detects operating parameters of the snow groomer vehicle 1, such as, for example, but not exhaustively, the power supplied by the drive unit 5; the power absorbed by each of the user devices, in particular the blade 8 and the tiller 9; the position of the blade 8 and the tiller assembly 9; and the speed of travel of the snow groomer vehicle 1.

Moreover, the control system 15 can detect one or more of the operating parameters of the snow groomer vehicle 1 selected from the following operating parameters of the tiller assembly 9: speed and/or direction of rotation of the shaft 9d; depth and/or cutting angle of the tiller assembly 9, preferably of the tiller 9a; position of the tiller assembly 9a along a vertical axis 71; mode for adjusting the position of the tiller assembly 9 along a vertical axis 71, preferably among a mode wherein the tiller assembly 9 is in a fixed position, a mode wherein the tiller assembly 9 exerts a certain pressure on the snowpack 72 in addition to its own weight or by subtraction from its own weight and said pressure value exerted, and a mode wherein the tiller assembly 9 is in a floating position, in particular in the floating position it follows the snowpack 72; position of the wings 9e, open or closed; volume of a working chamber of the tiller 9a; position of the tiller 9a with respect to a horizontal plane 73; mode of adjustment of the position of the tiller 9a in relation to a horizontal plane 73 preferably between a mode wherein the tiller assembly 9 is in a fixed position, and a mode wherein the tiller assembly is in a floating position, in particular in the floating position it follows the movements of the snow groomer vehicle 1; and position of the finisher 9b.

Moreover, in the above-described embodiment wherein the tiller assembly 9 comprises two tillers 9a connected to each other by a preferably universal joint, the control system 15, in addition to the above, can also detect, among the one or more of the operating parameters of the group of parameters described above, the mode of adjustment of the relative position of the two tillers 9a in the tiller assembly 9, in particular among: a mode wherein the relative position of the two tillers 9a is free and consequently the two tillers 9a are free to move independently of each other, a mode wherein the position of the two tillers 9a is fixed so that the two tillers 9a form a given angle of 180° lying in a plane oblique to the snowpack 72, in particular, the angle faces the snowpack 72, a mode wherein the position of the two tillers 9a is fixed so that the two tillers 9a form an angle of less than 180° lying in a plane incident to the snowpack 72, in particular, the angle faces the snowpack 72, and a mode wherein the position of the two tillers 9a is fixed so that the two tillers 9a form an angle of more than 180° lying in a plane incident to the snowpack 72, in particular, the angle faces the snowpack 72.

The control system 15 is equipped with wireless connection capability, for example, directly through a local communication network or through a mobile data network and an Internet connection, for connection to a resource management system of a ski resort, not shown here.

In particular, the snow groomer vehicle 1 comprises a radio-wave communication unit 18 coupled to the control system 15 for sending information received from remote to the control system 15 or for sending information from the control system 15 to the outside.

The blade 8 is connected to the frame 2 by a front connecting device 20, whereas the tiller assembly 9 is connected to the frame 2 by a rear connecting device 21.

The actuation command 11 is configured to control the front connecting device 20, is housed in the cab 3, and allows the positions of the blade 8 to be controlled.

In addition, the actuation command 11 is configured to control the rear connecting device 21 and is housed in the cab 3.

With reference to FIGS. 1 and 2, the rear connecting device 21 further comprises an actuator assembly 50 (FIG. 2) for controlling one or more of the following parameters of the tiller assembly 9: speed and/or direction of rotation of the shaft 9d; depth and/or cutting angle of the tiller assembly 9, preferably of the tiller 9a; position of the tiller assembly 9a along a vertical axis 71; mode for adjusting the position of the tiller assembly 9 along a vertical axis 71, preferably among a mode wherein the tiller assembly 9 is in a fixed position, a mode wherein the tiller assembly 9 exerts a certain pressure on the snowpack 72 in addition to its own weight or by subtraction from its own weight and said pressure value exerted, and a mode wherein the tiller assembly 9 is in a floating position, in particular in the floating position it follows the snowpack 72; position of the wings 9e, open or closed; volume of a working chamber of the tiller 9a; position of the tiller 9a with respect to a horizontal plane 73; mode of adjustment of the position of the tiller 9a in relation to a horizontal plane 73 preferably between a mode wherein the tiller assembly 9 is in a fixed position, and a mode wherein the tiller assembly is in a floating position, in particular in the floating position it follows the movements of the snow groomer vehicle 1; and position of the finisher 9b.

Moreover, in the above-described embodiment wherein the tiller assembly 9 comprises two tillers 9a connected to each other by a preferably universal joint, the actuator assembly 50 (FIG. 2), in addition to the above, can also control, among the one or more of the following parameters of the group of parameters described above, the mode of adjustment of the relative position of the two tillers 9a in the tiller assembly 9, preferably among: a mode wherein the relative position of the two tillers 9a is free and consequently the two tillers are free to move independently of each other, a mode wherein the position of the two tillers 9a is fixed so that the two tillers 9a form a given angle of 180° lying in a plane oblique to the snowpack 72, in particular, the angle faces the snowpack 72, a mode wherein the position of the two tillers 9a is fixed so that the two tillers 9a form an angle of less than 180° lying in a plane incident to the snowpack 72, in particular, the angle faces the snowpack 72, and a mode wherein the position of the two tillers 9a is fixed so that the two tillers 9a form an angle of more than 180° lying in a plane incident to the snowpack 72, in particular, the angle faces the snowpack 72.

The actuation command 11 is configured to control the rear connecting device 21 and the actuator assembly 50 of the tiller assembly 9. This actuation command 11 is housed in the cab 3 and allows one or more of the described operating parameters to be adjusted.

In one embodiment, the actuation command 11 for controlling the blade 8, in particular the front connecting device 20, and the actuation command 11 for controlling the tiller assembly 9, in particular the actuator assembly 50 of the tiller assembly 9 and the rear connecting device 21, are generally defined by a single manual control device which is a joystick with a lever and a series of mini-levers and push-buttons on the lever.

The control system 15 comprises a control device 17 coupled to the tiller assembly 9 and configured to control at least two parameters A and B of the tiller assembly 9, preferably five parameters A, B, C, D, and E, selected from the group comprising the following parameters of the tiller assembly 9: speed and/or direction of rotation of the shaft 9d; depth and/or cutting angle of the tiller assembly 9, preferably of the tiller 9a; position of the tiller assembly 9a along a vertical axis 71; mode for adjusting the position of the tiller assembly 9 along a vertical axis 71, preferably among a mode wherein the tiller assembly 9 is in a fixed position, a mode wherein the tiller assembly 9 exerts a certain pressure on the snowpack 72 in addition to its own weight or by subtraction from its own weight and said pressure value exerted, and a mode wherein the tiller assembly 9 is in a floating position, in particular in the floating position it follows the snowpack 72; position of the wings 9e, open or closed; volume of a working chamber of the tiller 9a; position of the tiller 9a in relation to a horizontal plane 73; mode of adjustment of the position of the tiller 9a in relation to a horizontal plane 73, preferably between a mode wherein the tiller assembly 9 is in a fixed position, and a mode wherein the tiller assembly is in a floating position, in particular in the floating position it follows the movements of the snow groomer vehicle 1; and position of the finisher 9b.

Moreover, in the above-described embodiment wherein the tiller assembly 9 comprises two tillers 9a connected to each other by a preferably universal joint, the control device 17 coupled to the tiller assembly 9, in addition to the above, can control at least two parameters A and B of the tiller assembly 9, in particular at least five parameters A, B, C, D and E, selected from the group of parameters described above which, in addition, also includes the mode of adjustment of the relative position of the two tillers 9a in the tiller assembly 9, preferably among: a mode wherein the relative position of the two tillers is free and consequently the two tillers are free to move independently of each other; a mode wherein the position of the two tillers 9a is fixed so that the two tillers 9a form a given angle of 180° lying in a plane oblique to the snowpack 72, in particular, the angle faces the snowpack 72; a mode wherein the position of the two tillers is fixed so that the two tillers 9a form an angle of less than 180° lying in a plane incident to the snowpack 72, in particular, the angle faces the snowpack 72; and a mode wherein the position of the two tillers 9a is fixed so that the two tillers 9a form an angle of more than 180° lying in a plane incident to the snowpack 72, in particular, the angle faces the snowpack 72.

In addition, the control device 17 includes a memory 19 configured to store at least two groups of values N and M, preferably four groups of values N, M, P, Q, relating to the at least two parameters A and B, wherein each group of values includes at least one value for each of the at least two parameters A and B.

In a preferred embodiment, each group of values N, M includes a first value N', M' and a second value N", M" for each of the at least two parameters A and B. The first value N', M' is associated with an upward movement of the snow groomer 1 and the second value N", M" is associated with a downward movement of the snow groomer 1.

The control device 17 is configured to receive the selection of a group of values of the at least two groups of values N and M, preferably four groups of values N, M, P, Q, and control the at least two parameters A and B of the tiller assembly according to the values $N_A$ and $N_B$ or $M_A$ and $M_B$ of the selected group of values.

Furthermore, the control device 15 is configured to receive information regarding the upward movement of the snow groomer vehicle 1 or the downward movement of the snow groomer 1 and control the at least two parameters by using the first value N', M' or the second value N", M" for each group of values of the at least two parameters according to the information received regarding the upward or downward movement of the snow groomer vehicle.

In greater detail, the selection among the groups of values N and M or N, M, P and Q, and the selection among the first value N' (or M', P' and Q') and the second value N" (or M", P" and Q") can be made in several ways.

In one embodiment, the selection among the groups of values is made through the user interface, in particular, the user interface comprises a selection command 39 for receiving a selection from the operator. The selection command 39 may be a key or a series of keys or may be the touch sensing device of a touch screen on which the different groups of selectable values are displayed. In other words, in this embodiment, the operator manually selects which group of values among the two groups of values N and M (or the four groups of values N, M, P and Q) he/she wants to use through the selection command 39 of the snow groomer vehicle 1.

Preferably, each of the two groups of values N and M (or the four groups of values N, M, P and Q) is associated with a respective snow condition different from the other, for example, fresh snow, spring snow, compact snow, or a customizable profile. As a result, the operator can see these groups of values associated with these different snow conditions on the user interface, particularly on the screen, and select by means of a key or directly on the screen, in the case of a touch screen, the current snow condition and therefore which group of parameter values to use.

In addition, the operator can send the information concerning the downward or upward movement of the snow groomer vehicle 1 to the control device 17 via the user interface, and consequently select whether to use the first value of the selected group of values of the parameters A, B (or A, B, C, D, E) or the second value of the selected group of values of the parameters A, B (or A, B, C, D, E).

In an alternative embodiment, the control device 17 is configured to control any number greater than two of parameters A, B, C, . . . of the tiller assembly 9 selected from the above-mentioned group of parameters.

In an alternative embodiment, the user, via the user interface, can select the number and type of parameters A, B, C, . . . to be controlled in automatic mode at any time.

In an alternative embodiment, the memory 19 of the control device 17 is configured to store any number of groups of values greater than two relating to any number of parameters greater than two, wherein each group of values comprises at least one value, preferably two values, for each of the parameters.

As stated above, the selection of the group of values N, M, P, Q and of the first or second X', X" value of the group of values N, M, P, Q can be done manually through the user interface and preferably the selection command 39, or it can be done automatically as shown below, or with a combination of manual and automatic.

In a preferred embodiment, the snow groomer vehicle 1 includes a detection device 40 to detect the upward or downward movement of the snow groomer vehicle 1 connected in communication with the control device 17 and to send to the control device 17 information regarding the upward or downward movement of the snow groomer vehicle 1, and wherein the control device 17 controls the at least two parameters by selecting the first or second value X', X" for each group of values N, M, P, Q of the at least two parameters A, B based on the information received from the detection device 40 regarding the upward or downward movement of the snow groomer vehicle 1.

In a preferred embodiment, the detection device 40 comprises an inclinometer and/or the satellite tracking device 13.

In a preferred embodiment, the snow groomer vehicle 1 comprises a detection device 41 for detecting the snow condition coupled in communication with the control device 17 to send information regarding the snow condition, so that the control device 17 selects one of the two groups of values based on the detected snow condition. In this case, therefore, the selection of the snow condition takes place automatically and without the intervention of the operator.

In a preferred embodiment, the detection device 41 for detecting the snow condition comprises at least one of the devices selected from the following group of devices: snow temperature sensor; ambient temperature sensor; sensor for the water percentage of the snow; ambient humidity sensor; snow density sensor; ambient light brightness sensor; a camera framing the snow surface; a thermo-camera framing the snow surface.

In a preferred embodiment, the snow groomer vehicle 1 comprises the radio frequency communication unit 18 configured to receive data relating to weather conditions and/or the current calendar date. The communication unit 18 is coupled in communication with the control device 17 to send information concerning the weather condition and/or the current date. The control device 17 receives the information concerning the weather condition and/or the current calendar date and selects one of the two groups of values N or M (or one of the four groups of values N, M, P or Q) based on the received weather condition and/or current calendar date.

In a preferred embodiment, the control device 17 is configured to receive at least one datum relating to the snow condition from remote via the communication unit 18, For example, a ski resort operator can send from remote the datum relating to the snow condition and/or to which group of values to use among the two groups of values N and M, or among the four groups of values N, M, P and Q. In this case, the control device 17 is configured to select one of the two groups of values N, M (or of the four groups of values N, M, P and Q) based on the datum received from remote.

In a preferred embodiment, the control device 17 comprises a counting unit 42 for counting the calendar date and the control device 17 selects one of the groups of values N, M based on the calendar date provided by the calendar date counting unit 42.

In a preferred embodiment, the user interface is coupled to the control device 17 and is configured to receive a selection regarding the snow condition.

Figure 6:
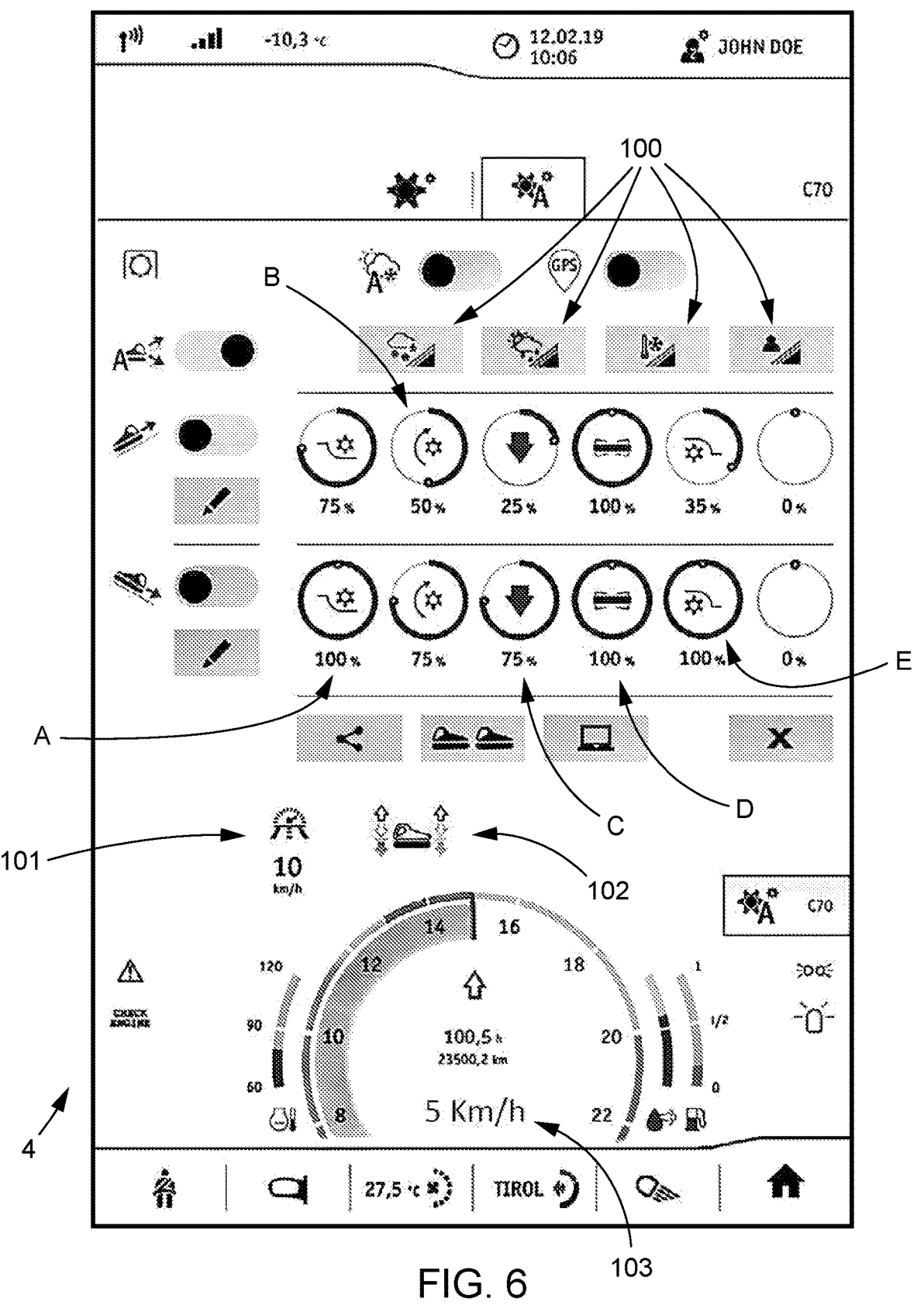
FIG. 6 shows a display screen of the snow groomer vehicle made according to an embodiment of the present invention.

In particular, FIG. 6 shows an exemplary display screen 4 of a preferred embodiment, on which the selectable snow conditions 100 are displayed. In particular, in the non-limiting example shown in FIG. 6, the following conditions are displayed: fresh snow, spring snow, compact snow, or a customizable profile.

As said before, each of the snow conditions 100 is associated with a respective group of values N, M, P, Q.

Through the display screen 4, the operator selects the snow condition that he/she believes is most appropriate and consequently selects which group of values to use among the groups of values.

Furthermore, the display screen 4 depicted in FIG. 6 shows the values of the selected group of values and the parameters A, B, C, D, E which can be controlled in automatic mode.

Moreover, the display screen 4 in FIG. 6 also shows the two different values of the parameters A, B, C, D, E when the snow groomer vehicle 1 is moving upwards and when it is moving downwards. In this case, the display screen 4 indicates whether the automatic mode of detection of the upward or downward movement of the snow groomer vehicle 1 is active or whether the upward or downward movement mode has been selected by the operator.

Moreover, the display screen is configured to indicate the optimal speed value 101 associated with the values of the parameters currently in use and/or the optimal suspension setting value 102 associated with the values of the parameters currently in use. Preferably, the display screen 4 is also configured to display in the same screenshot the current forward speed 103 of the snow groomer vehicle 1.

In this way, the operator can adjust the speed of the snow groomer vehicle 1 by acting on the travel control 10 to move at the optimal speed and/or set the suspension parameters to the optimal values.

In a preferred embodiment, the display screen 4 is a touch screen, i.e., a touch sensitive screen, consequently the operator can directly select via the display screen 4, by touching said display screen 4, one or more of the following selections: snow condition; automatic mode of detection of the upward or downward movement; manual mode of detection of the upward or downward movement; select whether to use the upward or downward movement values; and change the values of each group of values. In this embodiment, the selection command 39 is preferably defined by the touch screen of the display screen 4.

In all the embodiments, the control device 17 receives the information concerning the snow condition and selects one of the groups of values N, M (N, M, P, Q) based on the selection of the snow condition received.

Furthermore, in a preferred embodiment, the plurality of groups of values comprises an additional group of values which is associated with artificial snow. As a result, the groups of values will be three or five, or a number equal to or greater than three. In this embodiment, the group of values comprising parameters suitable for processing artificial snow can be selected manually by the operator or, in a preferred embodiment, in an automatic or semi-automatic manner. In one embodiment, the snow groomer vehicle 1 is coupled to devices for producing artificial snow or to a ski resort management system which, in turn, is coupled to devices for producing artificial snow. In this preferred embodiment, when the automatic mode is selected, the control device 17 is configured to use the third (or fifth) group of values, which is associated with artificial snow, when it receives the information from remote via the artificial snow-producing devices or from the ski resort to which it is coupled.

In addition, each value of the group of values can be changed by the operator via the user interface, for example, the selection command or the actuation command 11, but only when the snow groomer vehicle 1 is stationary. For this purpose, the control device 17 is configured to receive modification of the values of each group of values of the parameters by the operator and to modify each value of the group of values of the parameters. Moreover, the control system 15 enables the control device 17 to modify the parameters only after having detected that the snow groomer vehicle 1 is stationary and having placed the snow groomer vehicle 1 in a mode for locking the tracks and the user devices.

Moreover, the actuation command 11 is always active and operative during the operation of the snow groomer vehicle 1, therefore, during the operation, the operator can act on the parameters to modify the parameters currently set in automatic mode. In this case, the snow groomer vehicle 1, for that parameter that has been modified, will no longer use an automatic adjustment but will follow the manual adjustment set by the operator until the snow groomer vehicle 1 is switched off or until the operator via the user interface enters the automatic mode for that parameter too.

In a preferred embodiment, in the manual mode, in which the operator manually sets the values of the group of values to be used through the user interface, the control device 17 stores the values of the group of values set by the operator during its operation and associates them with other detected parameters, such as, for example, weather, snow temperature, ambient temperature, snow density, water content of the snow, brightness, inclination, position of the snow groomer vehicle 1 within the ski resort, and defines a coupling between the values of the group of values selected by the operator and the detected parameters. In a preferred embodiment, the control device 17 is configured to work in automatic mode using the values of the group of values coupled to the parameters it had previously coupled and stored.

In other words, the user interface 4 is configured to allow an operator to set each at least one value of the at least two groups of values of the at least one parameter. And the control device 17 is configured to record, in one operating mode, the at least one value entered by the operator through the user interface and associate it with one or more of the following detected parameters: a position of the snow groomer vehicle, temperatures and/or humidity of the air and/or snow, weather data received. The control device 17 is configured to set, in another operating mode, the at least one value, set in the first operating mode, of each group of values based on the data recorded in the first operating mode and on one or more of the following parameters detected: a position of the snow groomer vehicle, temperatures and/or humidity of the air and/or snow, weather data received.

In one embodiment, the control device 17 stores the parameters that are used by the operator in manual mode and sends them to a remote central unit of a ski resort, the remote central unit analyses the data and defines the values of the parameters of the group of values. In the semi-automatic mode, the operator can select one of the groups of values N, M, P, Q autonomously and the control device 17 couples them to the detected data, temperature, humidity etc., and uses them for the fully automatic mode.

In a preferred embodiment, the invention comprises a fleet of snow groomer vehicles comprising two or more snow groomer vehicles.

Each of the snow groomer vehicles 1 is configured to exchange data via the communication unit 18 and the control device 17 is configured to send the selection of the group of values to be used at a given point on the slope to the other snow groomer vehicle(s) 1. The other snow groomer vehicle(s) is/are configured to receive the selection of the group of values and display this selection on the screen to send a message to the operator. Through the selection device, the operator can choose whether to use the group of values received from remote or the pre-set ones he/she has on his/her snow groomer vehicle 1. In an alternative embodiment, each control device 17 controls the parameters of the tiller assembly based on the selected group of values it has received.

In a preferred embodiment, the ski resort comprises a remote central unit. Both in manual mode and in automatic or semi-automatic mode, each snow groomer vehicle 1 sends data to the ski resort's remote central unit which analyses the data of each snow groomer vehicle 1 of the fleet of snow groomer vehicles 1.

In greater detail, each control device 17 stores the values of the group of values selected by the operator during its use and associates them with other detected parameters, such as, for example, weather, snow temperature, ambient temperature, snow density, water content of the snow, brightness, inclination, position provided by the satellite tracking device 13 within the ski resort. Each control device defines a coupling between the values of the group of values selected by the operator and the detected parameters and sends them to the remote central unit. The remote central unit analyses the data received from the plurality of control devices and processes such data, for example by using statistical functions such as mean, median, variance, and defines the values of the groups of values to be used in automatic mode.

In a preferred embodiment, the control device 17 is configured to work in automatic mode using the values of the group of values coupled to the parameters it had previously coupled and stored.

In a preferred embodiment, the snow groomer vehicle 1 is configured to be started via a user code. The control device 7 stores in the memory at least a first user code and a second user code. The control device 7 is configured to detect a user code entered through the user interface by an operator when starting the snow groomer vehicle 1 and to enable or not the sending of data to other snow groomer vehicles 1 based on the user code entered between the first and second user codes.

In a preferred embodiment, the snow groomer vehicle 1 is configured to be started via a user code. The control device 17 stores in the memory at least a third user code and a fourth user code. The control device 17 is configured to detect a user code entered through the user interface by an operator when starting the snow groomer vehicle 1 and to enable or not the variation of the values of the groups of values of the control device.

In a preferred embodiment, the snow groomer vehicle 1 is configured to be started via a user code. The control device 17 stores in the memory at least a fifth user code and a sixth user code. The control device 17 is configured to detect a user code entered through the user interface by an operator when starting the snow groomer vehicle 1 and to enable or not the selection among manual, automatic or semi-automatic control, in other words, on the basis of the entered user code, the control device 17 can enable the use of the manual control alone or can enable the use of the automatic and/or semi-automatic control alone, or can enable all the control modes.

As can be understood from the description, the invention can be extended to any number of parameters greater than or equal to two, in FIG. 5, for example, the invention is illustrated using five parameters A, B, C, D and E, but the number of parameters can be two A, B, or six A, B, C, D, E and F, or any other number greater than one. Increasing the number of parameters increases the automation efficiency of the snow groomer vehicle 1 and consequently increases the ease for the driver to drive the snow groomer vehicle.

The number of groups of values N, M, . . . , Z can be any number greater than or equal to two, and what has been mentioned above for two groups of values or four groups of values applies for any number of groups of values greater than or equal to two.

In a preferred embodiment, the control device 17 comprises a number of user codes greater than two selected from the user codes illustrated above, accordingly, it may include the six user codes illustrated above or four user codes illustrated above, or a combination of user codes with the functions illustrated above.

In a preferred, non-limiting embodiment of the present invention, the tiller assembly 9 of the snow groomer vehicle 1 comprises two tillers 9a which are connected to each other by a preferably universal joint, and the parameters controlled by the control device 17, according to the modes illustrated above, are the following parameters: speed and/or direction of rotation of the shafts 9d; depth or cutting angle of the tiller assembly 9, preferably of the tillers 9a; mode for adjusting the position of the tiller assembly 9 along a vertical axis, preferably among: a mode wherein the tiller assembly 9 is in a fixed position, a mode wherein the tiller assembly exerts a certain pressure on the snowpack 72 in addition to its own weight or by subtraction from its own weight and said pressure value exerted, and a mode wherein the tiller assembly 9 is in a floating position, in particular in the floating position it follows the snowpack 72; volume of a working chamber of the tillers 9a; mode of adjustment of the relative position of the two tillers 9a in the tiller assembly 9, preferably among: a mode wherein the relative position of the two tillers 9a is free and consequently the two tillers 9a are free to move independently of each other, a mode wherein the position of the two tillers 9a is fixed so that the two tillers 9a form a given angle of 180° lying in a plane oblique to the snowpack 72, in particular, the angle faces the snowpack 72, a mode wherein the position of the two tillers is fixed so that the two tillers 9a form an angle of less than 180° lying in a plane incident to the snowpack 72, in particular, the angle faces the snowpack 72, and a mode wherein the position of the two tillers 9a is fixed so that the two tillers 9a form an angle of more than 180° lying in a plane incident to the snowpack 72, in particular, the angle faces the snowpack 72.

In another preferred, non-limiting embodiment of the present invention, the tiller assembly 9 of the snow groomer vehicle 1 comprises two tillers 9a which are connected to each other by a preferably universal joint, and the parameters controlled by the control device 17, according to the modes illustrated above, are the following parameters: speed and/or direction of rotation of the shafts 9d; depth or cutting angle preferably of the tillers 9a; mode for adjusting the position of the tiller assembly 9 along a vertical axis, preferably among: a mode wherein the tiller assembly 9 is in a fixed position, a mode wherein the tiller assembly exerts a certain pressure on the snowpack 72 in addition to its own weight or by subtraction from its own weight and said pressure value exerted, and a mode wherein the tiller assembly 9 is in a floating position, in particular in the floating position it follows the snowpack 72; position of the finisher 9b; mode of adjustment of the relative position of the two tillers 9a in the tiller assembly 9, preferably among: a mode wherein the relative position of the two tillers 9a is free and consequently the two tillers 9a are free to move independently of each other; a mode wherein the position of the two tillers 9a is fixed so that the two tillers 9a form a given angle of 180° lying in a plane oblique to the snowpack 72, in particular, the angle faces the snowpack 72, a mode wherein the position of the two tillers 9a is fixed so that the two tillers 9a form an angle of less than 180° lying in a plane incident to the snowpack 72, in particular, the angle faces the snowpack 72, and a mode wherein the position of the two tillers 9a is fixed so that the two tillers 9a form an angle of more than 180° lying in a plane incident to the snowpack 72, in particular, the angle faces the snowpack 72.

The invention claimed is:

1. A snow groomer vehicle comprising:
a frame (2) extending along a longitudinal axis (70);
a tiller assembly (9) connected to the frame (2) by a connecting device (21), the tiller assembly (9) comprising at least a tiller (9a) and a finisher (9b);
at least one control device (17) coupled to the tiller assembly (9) and configured to control at least two parameters of the tiller assembly (9), the at least two parameters selected from a group consisting of parameters of the tiller assembly (9):
speed and/or direction of rotation of a shaft (9d);
depth and/or cutting angle of the tiller (9a);
position of the tiller assembly (9a) along a vertical axis (71); and
a mode for adjusting the position of the tiller assembly (9) along the vertical axis (71), selected from:
a mode wherein the tiller assembly (9) is in a fixed position,
a mode wherein the tiller assembly (9) exerts a certain pressure on the snowpack (72) in addition to the tiller assembly's own weight or by subtraction from the tiller assembly's own weight and said pressure value exerted, and
a mode wherein the tiller assembly (9) is in a floating position, and the floating position follows the snowpack (72);
position of wings (9e) open or closed;

volume of a working chamber of the tiller (9*a*);
> position of the tiller (9*a*) in relation to a horizontal plane (73);
> mode of adjustment of the position of the tiller (9*a*) in relation to the horizontal plane (73) wherein the mode of adjustment is between a mode wherein the tiller assembly (9) is in the fixed position, and a mode wherein the tiller assembly is in a floating position; and
> position of the finisher (9*b*);
> the control device (17) includes a memory (19) configured to store at least two groups of values (N, M), relating to the at least two parameters, wherein each group of values (N, M) includes at least one value for each of the at least two parameters;
> the control device (17) being configured to receive a selection of a group of values of the at least two groups of values (N, M) and control the at least two parameters of the tiller assembly (9) according to the values of the selected group of values (N; M).

2. The snow groomer vehicle according to claim 1, wherein each group of values (N, M) includes a first value (N', M') and a second value (N", M") for each of the at least two parameters; wherein the first value (N', M') is associated with an upward movement of the snow groomer vehicle (1) and the second value (N", M") is associated with a downward movement of the snow groomer vehicle (1).

3. The snow groomer vehicle according to claim 2, wherein the control device (17) is configured to receive information regarding the upward movement of the snow groomer vehicle (1) or the downward movement of the snow groomer vehicle (1) and control the at least two parameters by using a first or second value (N', N"; M', M") for each group of values of the at least two parameters according to information received regarding the movement of the snow groomer (1).

4. The snow groomer vehicle according to claim 1, wherein the snow groomer vehicle (1) includes a user interface configured to receive information from a user regarding downward or upward movement of the snow groomer (1); and wherein the control device (17) is coupled to the user interface to receive the information and control the at least two parameters by using a first or second value for each group of values (N', M'; N", M") of the at least two parameters based on the information received from the user interface.

5. The snow groomer vehicle according to claim 1, wherein the snow groomer vehicle (1) includes a first detection device (40) to detect upward or downward movement of the snow groomer vehicle (1) connected in communication with the control device (17) and to send to the control device (17) information regarding the upward or downward movement of the snow groomer vehicle (1), and wherein the control device (17) controls the at least two parameters by using the first or second value for each group of values (N, M) based on the information received from the first detection device (40); wherein the first detection device (40) includes an inclinometer and/or a satellite tracking device (13).

6. The snow groomer vehicle according to claim 1, wherein each of the at least two groups of values (N, M) is associated with a respective snow condition different from the other; the snow groomer vehicle (1) includes a second detection device to detect the snow condition, and is coupled in communication with the control device (17) to send information regarding the snow condition, and wherein the control device (17) receives the information regarding the snow condition and selects one of the at least two groups of values (N, M) according to the detected snow condition; wherein the second detection device (41) for detecting the snow condition includes at least one device selected from the following group of devices: snow temperature sensor; ambient temperature sensor; sensor for the water percentage of the snow; ambient humidity sensor; light sensor; a camera framing a snow surface; a thermo-camera framing the snow surface.

7. The snow groomer vehicle according to claim 1, wherein each of the at least two groups of values (N, M) is associated with a respective snow condition different from the other; the snow groomer vehicle (1) comprising a user interface coupled to the control device (17) and configured to receive a selection regarding a snow condition; and wherein the control device (17) receives the information regarding the snow condition and selects one of the at least two groups of values (N, M) according to the snow condition received.

8. The snow groomer vehicle according to claim 1, wherein each of the at least two groups of values (N, M) is associated with a respective snow condition different from the other; the snow groomer vehicle (1) includes a radio frequency communication unit (18) configured to receive data regarding weather conditions and/or the current calendar date; the communication unit (18) being coupled in communication with the control device (17) to send information regarding weather conditions and/or current calendar date, and wherein the control device (17) receives the information regarding the weather condition and/or current calendar date and selects one of the at least two groups of values (N, M) based on the received data regarding weather conditions and/or current calendar date.

9. The snow groomer vehicle according to claim 1, wherein each of the two groups of values (N, M) is associated with a respective snow condition different from the other; wherein the control device (17) includes a counting unit (42) for counting calendar dates; wherein the control device (17) selects one of the two groups of values according to the calendar date provided by the counting unit (42) for counting the calendar date.

10. The snow groomer vehicle according to claim 1, wherein the snow groomer vehicle (1) includes a radio frequency communication unit (18) configured to receive data, the communication unit (18) being coupled in communication with the control device (17) to send the selection of the group of values (N, M) to be used, and wherein the control device (17) receives the selection of the group of values to be used and controls the parameters of the tiller assembly according to the at least one value of the group of values selected and received through the communication unit (8).

11. The snow groomer vehicle according to claim 1, wherein the control device (17) is configured to record, in a first operating mode, an operator's selections via a user interface and associate them with one or more of the following parameters: a position of the snow groomer vehicle, temperatures and/or humidity of the air and/or snow, and weather data received; the control device (17) being configured to select, in a second operating mode, one group of values from the at least two groups of values (N,M) based on the data recorded in the first operating mode and one or more of the following parameters detected: a position of the snow groomer vehicle, temperature and/or humidity of the air and/or snow, and weather data received.

12. The snow groomer vehicle according to claim 1, comprising a user interface (4) configured to allow an operator to set each at least one value of the at least two groups of values of at least one parameter; wherein the control device (17) is configured to record, in one operating mode, at least one value entered by the operator through the user interface and associate the at least one value with one or more of the following parameters: a position of the snow groomer vehicle, temperature and/or humidity of the air and/or snow, and weather data received; the control device (17) being configured to set, in another operating mode, the at least one value, set in the first operating mode, of each group of values based on data recorded in the first operating mode and on one or more of the following parameters detected: a position of the snow groomer vehicle, temperatures and/or humidity of the air and/or snow, and weather data received.

13. The snow groomer vehicle according to claim 1, wherein the control device (17) is configured to store a plurality of user codes and enable sending of data to other snow groomer vehicles and/or the operating mode of the snow groomer vehicle among manual, semi-automatic and automatic and/or the setting of the values of each group of values according to user codes entered by an operator through a user interface when starting the snow groomer vehicle.

14. The snow groomer vehicle according to claim 1, wherein the tiller assembly (9) includes another tiller (9a) connected to the tiller (9a) via a universal joint; wherein the group of parameters of the tiller assembly (9) includes: a mode for adjusting a relative position of the two tillers (9a) in the tiller assembly (9) among: a mode wherein the relative position of the two tillers is free and consequently the two tillers are free to move independently of each other; a mode wherein the position of the two tillers is fixed so that the two tillers (9a) form an angle of 180° towards the snow groomer vehicle (1); a mode wherein the position of the two tillers is fixed so that the two tillers (9a) form an angle of less than 180° towards the snow groomer vehicle (1); and a mode wherein the position of the two tillers (9a) is fixed so that the two tillers (9a) form an angle of more than 180° towards the snow groomer vehicle (1).

15. The snow groomer vehicle according to claim 1, wherein parameters controlled by the control device (17) are at least the following:

speed and/or direction of rotation of the shafts (9d);

depth or cutting angle of the tillers (9a);

mode for adjusting the position of the tiller assembly (9) along a vertical axis, among: a mode wherein the tiller assembly (9) is in the fixed position, a mode wherein the tiller assembly exerts a certain pressure on the snowpack (72) in addition to the tiller assembly's own weight or by subtraction from the tiller assembly's own weight and said pressure value exerted, and a mode wherein the tiller assembly (9) is in a floating position, in in the floating position it follows the snowpack (72);

volume of a working chamber of the tillers (9a); and position of the finisher (9b).

16. A snow groomer vehicle according to claim 1, comprising a display screen (4) coupled to the control device (17) and configured to illustrate: values of the group of values of the parameters in use, and an optimal travel speed (101) associated with the values of the parameters in use, and an optimal configuration of a set-up (102) of the suspensions, of the snow groomer vehicle (1) associated with the values of the parameters currently in use.

17. A snow groomer vehicle according to claim 1, comprising a display screen (4) coupled to the control device (17) and configured to illustrate the user-selectable snow conditions (100) associated the different groups of values and the values of the parameters associated with each different snow condition and with an upward or downward movement of the snow groomer vehicle (1).

18. A ski resort comprising a snow groomer vehicle in accordance with claim 1 and at least one artificial snow gun, the control device (17) being coupled in communication with the artificial snow gun to receive information regarding the activation or not of the artificial snow gun, the control device (17) being configured to select one of the groups of values based on information received from the at least one artificial snow gun.

19. A tracked vehicle fleet comprising at least two tracked vehicles according to claim 1, wherein the tracked vehicles (1) are coupled in communication through their respective radio frequency communication units (18); the control device (17) of one of the tracked vehicles is configured to send the selection of the group of values and/or the values of the group of values to the control device (17) of the other tracked vehicle (1) and the control devices (17) of the other tracked vehicle (1) control the parameters of the tiller assembly according to the group of values and/or the values received.

20. A control method for controlling a snow groomer vehicle; the snow groomer vehicle comprising: a frame (2) extending along a longitudinal axis (70); a tiller assembly (9) connected to the frame (2) by a connecting device (20), the tiller assembly (9) comprising a tiller (9a) and a finisher (9b);

the method comprising the steps of:

controlling at least two parameters of the tiller assembly (9), selected from a group consisting of parameters of the tiller assembly (9):

speed and/or direction of rotation of a shaft (9d);

depth and/or cutting angle of the tiller assembly (9) tiller (9a);

position of the tiller assembly (9a) along a vertical axis (71);

mode for adjusting the position of the tiller assembly (9) along the vertical axis (71), from among: a mode wherein the tiller assembly (9) is in a fixed position, a mode wherein the tiller assembly (9) exerts a certain pressure on the snowpack (72) in addition to the tiller assembly's own weight or by subtraction from the tiller assembly's own weight said pressure value exerted, and a mode wherein the tiller assembly (9) is in a floating position;

position of wings (9e) open or closed;

volume of a working chamber of the tiller (9a);

position of the tiller (9a) with respect to a horizontal plane (73);

mode of adjustment of the position of the tiller (9a) in relation to the horizontal plane (73) between a mode wherein the tiller assembly (9) is in the fixed position, and a mode wherein the tiller assembly is in a floating position, in the floating position the tiller assembly follows the movements of the snow groomer vehicle (1); and position of the finisher (9b);

storing at least two groups of values (N, M), relating to the at least two parameters, wherein each group of values (N, M) includes at least one value for each of the at least two parameters;

receiving a selection of a group of values of the at least two groups of values; and controlling the parameters of the tiller assembly (9) according to the values of the selected group of values.

21. A computer program configured to run in a processing unit and implement the steps of the method of claim 20.

22. A memory device in which the computer program of claim 21 is stored.

\*　\*　\*　\*　\*

20